United States Patent
Seeger et al.

(10) Patent No.: US 6,562,961 B1
(45) Date of Patent: May 13, 2003

(54) AMINOALKYL TRIALKYL SILYL CELLULOSE AND A METHOD FOR COATING SURFACES

(75) Inventors: Stefan Seeger, Bad Abbach (DE); Frank Loescher, Regensburg (DE)

(73) Assignee: Molecular Machines & Industries GmbH, Heidelberg (DE)

( * ) Notice: Subject to any disclaimer, the term of this patent is extended or adjusted under 35 U.S.C. 154(b) by 0 days.

(21) Appl. No.: 09/486,178

(22) PCT Filed: Aug. 24, 1998

(86) PCT No.: PCT/EP98/05365

§ 371 (c)(1),
(2), (4) Date: Jun. 7, 2000

(87) PCT Pub. No.: WO99/10383

PCT Pub. Date: Mar. 4, 1999

(30) Foreign Application Priority Data

Aug. 23, 1997 (DE) .......................... 197 36 736

(51) Int. Cl.[7] .................. C08B 11/02; C08B 11/145
(52) U.S. Cl. ............... 536/56; 536/30; 536/43; 536/44; 536/55.3; 536/57; 536/90; 536/99; 536/120; 536/124; 424/488
(58) Field of Search .................. 536/90, 99, 30, 536/43, 44, 55.3, 56, 57, 120, 124; 424/488

(56) References Cited

U.S. PATENT DOCUMENTS

| | | | | | |
|---|---|---|---|---|---|
| 4,413,121 A | * | 11/1983 | Brandt et al. | .................. | 536/44 |
| 4,474,950 A | * | 10/1984 | Felcht et al. | .................. | 536/85 |
| 5,004,808 A | * | 4/1991 | Yalpani et al. | .................. | 536/56 |
| 5,426,182 A | * | 6/1995 | Jenkins et al. | .................. | 536/54 |
| 2001/0021387 A1 | * | 9/2001 | Krammer et al. | .......... | 424/401 |

* cited by examiner

Primary Examiner—Samuel Barts
Assistant Examiner—Devesh Khare
(74) Attorney, Agent, or Firm—Foley & Lardner

(57) ABSTRACT

The invention relates to polysaccharide derivatives comprising a) at least one hydrophobic and b) at least one nitrogen-containing substituent; in particular, the derivative is a cellulose ether which, as substituent a), has a trialkylsilyl and, as substituent b), an aminoalkyl group.

Figure 1:
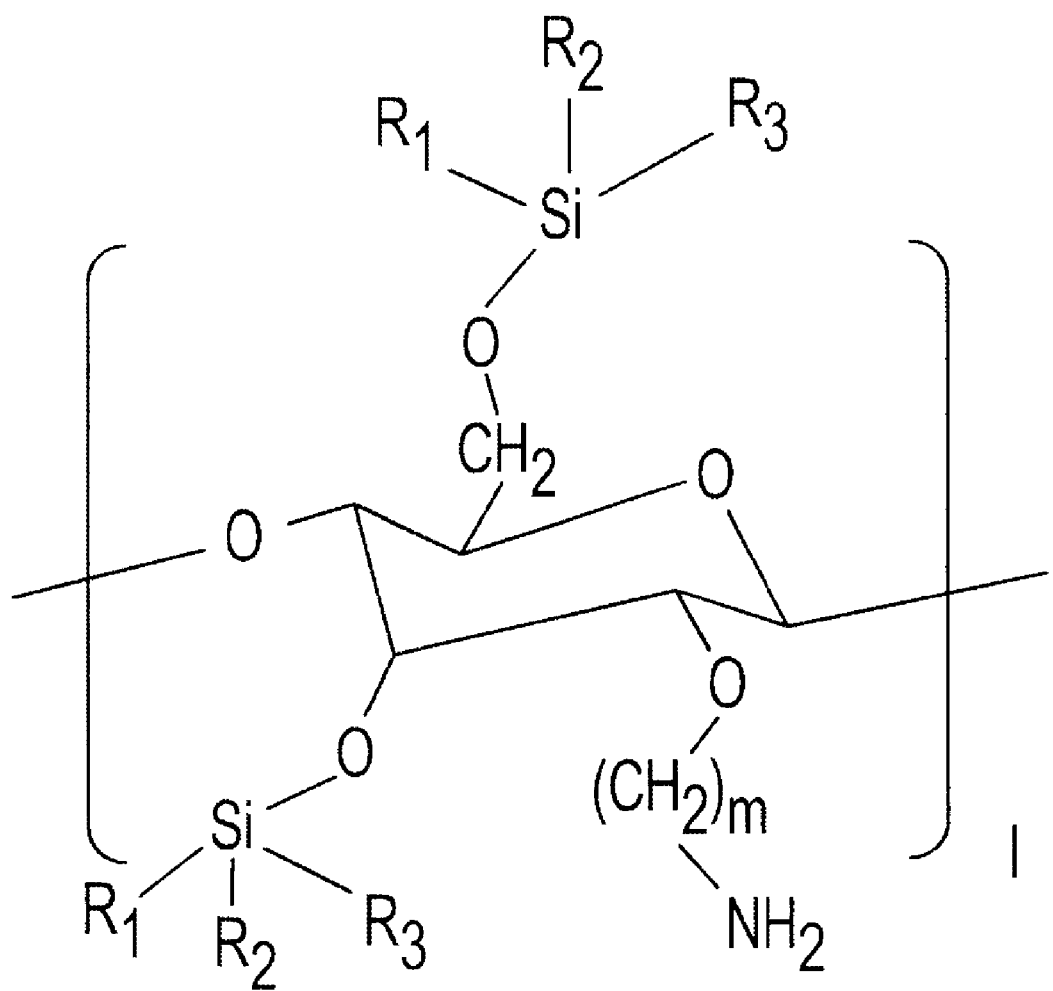

Furthermore, it relates to a process for immobilizing biomolecules on a coated sheet-like carrier material in which the biomolecules are attached at or in the coating and the coated sheet-like carrier material comprises within or outside the coating at least one such polysaccharide derivative.

Additionally, in the process for preparing the mixed cellulose ether a solution of trialkylsilylcellulose in an organic solvent is admixed with a reactive aminoalkane derivative which is insoluble or only sparingly soluble in this solvent, the reaction is carried out and the end product is isolated.

16 Claims, 1 Drawing Sheet

AMINOALKYL TRIALKYL SILYL CELLULOSE AND A METHOD FOR COATING SURFACES

This application is a rule 371 Application of PCT/EP 98/053,65, filed Aug. 24, 1998, which claims priority to German Patent Application No. 197,367,364, filed Aug. 23, 1997.

The invention relates to novel polysaccharide derivatives, such as cellulose ethers, i.e. in particular aminoalkyltrialkylsilylcelluloses, their preparation and their use in a process for coating surfaces with defined molecular layers.

The immobilization of biomolecules on solid carriers plays a decisive role in a large number of modern analysis and separation techniques, such as affinity chromatography, bioreactor technique and, in particular, bio- and chemosensory analysis.

For example, a detection in immunological tests and hybridization tests is carried out by specific reaction of receptor molecules adsorbed on a solid substrate surface with the species to be determined. In particular in the field of the highly sensitive detection of individual DNA, RNA, antigen and/or protein molecules, it is very important that the molecules in question are bound specifically and firmly to surfaces, and that unspecific adsorption of molecules at these substrate surfaces is prevented.

Various processes for binding biomolecules on solid substrate surfaces are known.

A simple option is adsorptive immobilization in which the binding on a substrate surface is purely by adsorption via non-covalent interaction. This method has various disadvantages. Immobilization is limited to substrates whose surface properties permit adsorptive binding and ensure sufficient stability. Gaps in the biomolecule layer may be formed by incomplete coating or desorption processes. Finally, control of both orientation and the amount of receptor molecules is unsatisfactory, so that it is difficult to achieve a reproducible preparation.

To avoid these disadvantages, there has been a quest for covalent immobilization processes which allow biomolecules to be bound covalently to solid substrates via functional groups. These covalent processes are based on bifunctional bridge reagents reacting both with the substrate surface and with the biomolecule.

These immobilization processes, which frequently proceed in several steps, are very time-and material-consuming. A further disadvantage of these methods is the formation of inhomogeneous polymeric surface structures, for example of silane films generated in practice, in the presence of moisture; see, for example, Joachim Renken et al., Anal. Chem. 1996, 68, pp. 176 to 182 in "Multifrequency Evaluation of Different Immunosorbents on Acoustic Plate Mode Sensors".

A further technique for coupling biomolecules on solid substrate surfaces is the self-assembly (SA) technique (see, for example, Kevin L. Prime et al., J. Amer. Chem. Soc. 1993, 115, pp. 10714 to 10721 in "Adsorption of Proteins onto Surfaces Containing End-Attached Oligo (ethylenoxide): A Model System Using Self-Assembled Monolayers"). Here, stable films of organic substances are formed by spontaneous self-assembly of the molecules during adsorption on solid substrates. The best-known SA systems are organic disulphides and thiols on gold surfaces. This method has the disadvantage that it is limited to only a few types of substrate, such as metals or specific oxides.

Related to the SA technique is the Langmuir-Blodgett (LB) technique. If suitable substances are spread on a surface of water, they spread out to form a monomolecular film. With the aid of this technique developed by Langmuir and Blodgett, it is possible to transfer these monomolecular films to solid substrates (see Katharine B. Blodgett et al., Physical Review, Vol. 51, June 1937, pp. 964 to 982 in "Built-Up Films of Barium Stearate and Their Optical Properties"). This process involves a very limited input of time and material.

Particularly ordered and stable films are obtained by using so-called non-arnphiphilic Stab-Haar polymers (for example M. Schaub et al., Thin Solid Films, 210/211, 1992, pp. 397 to 400 in "Investigation of molecular superstructures of hairy rodlike polymers by X-ray reflection").

During transfer to the solid substrate, the polymer rods orientate themselves in parallel to the dipping direction. A particularly high stability of the films can additionally be achieved by crosslinking alkene substituents present in the polymer in a [2+2]-cycloaddition with UV irradiation (Gerhard Wegner, Thin Solid Films, 216, 1992, pp. 105 to 116 in "Ultrathin Films of polymers: architecture, characterization and properties").

Cellulose derivatives having olefinic side chains have been used with particular success. After the film has been transferred to the substrate, these can be converted in a modified Lemieux oxidation into carbonyl groups to which biomolecules are coupled covalently as "Schiff bases" (WO-A 95/08770 or Frank Löscher et al., Proc. SPIE Vol. 2928, 1996, pp. 209 to 219).

By varying the length of time of exposure, it is additionally possible to vary the density of coverage. It is possible to couple biomolecules covalently to other cellulose derivatives having free amino or hydroxyl groups by using a bifunctional bridge reagent such as cyanuric chloride (see reference above).

This process has the disadvantage that it is limited to hydrophobic or hydrophobicized substrate types. Thus, hydrophilic glass or quartz substrates, for example, have to be hydrophobicized in complicated wet-chemical steps with the aid of, for example, silane derivatives prior to coating with hydrophobic LB substances.

Accordingly, it is the object of the invention to provide a process and a chemical compound suitable for this process allowing the application of at least one molecule layer onto a wide variety of different surfaces, independently of the hydrophilicity of surfaces.

This object is achieved on the one hand by polysaccharide derivatives, in particular cellulose derivatives having a degree of polymerization of >5, preferably mixed cellulose ethers comprising a) at least one hydrophobic and b) at least one nitrogen-containing substituent.

In preferred embodiments, the mixed cellulose ethers have, as substituent a), a trialkylsilyl and, as substituent b), an aminoalkyl group, where the alkyl radical in particular in the substituent a) has 1 or 2 C atoms and in the substituent b) has 2 to 8 C atoms. Additionally, the polysaccharide derivative may also comprise c) at least one further substituent which carries a group which is crosslinkable photochemically, by a free-radical reaction or thermally.

According to the present invention, the preferred mixed cellulose ethers are to be understood as compounds in which the H of individual OH groups of the cellulose skeleton is replaced by organic or organosilyl groups, i.e. the atom directly adjacent to the O is a C or Si. Furthermore, this expression can also include derivatives which additionally carry further substituents (in particular at the O of the OH group), an example of such an additional substituent being the substituent c). In the actual molecules (as information base, see Lothar Brandt in Ullmann's Encyclopedia of Industrial Chemistry, Vol. A5, 2nd edition, keyword "cellulose ethers", p. 461 ff.), it is not necessary for each individual molecule unit (anhydroglucose unit) in the cellulose ether molecule to be substituted at one or more OH groups, but the designation of the compound refers to the entirety of the molecules or molecule units, i.e. designates an average value; in general, a maximum of 3 OH groups per molecule unit can be substituted. For the preparation and/or the behaviour of cellulose derivatives comprising the substituents a) or c) (but not b)), reference is made to the literature reference above by Frank Löscher et al. and to Dieter Klemm et al., Z. Chem., 24 (1984), Vol. 2, p. 62 in "4-Dimethylamino-pyridin-katalysierte Synthese von Celluloseestern über organolösliche Synthese von Celluloseestern über organolösliche Trimethylcellulose".

The object of the invention is furthermore achieved starting with the known process for immobilizing biomolecules on a coated sheet-like carrier material in which the biomolecules are attached at or in the coating. In this case, the process according to the invention is characterized in that the coated sheet-like carrier material comprises within or outside the coating at least one of the abovementioned polysaccharide derivatives, in particular one of the mixed cellulose ethers.

Below, preferred embodiments of this process are illustrated in more detail.

To a solid surface, at least one monomolecular layer of the polysaccharide derivative is applied, where the polysaccharide derivative comprises, as substituent a), preferably a hydrophobic substituent having alkyl, alkenyl, aryl, alkylsilyl, alkenesilyl and/or arylsilyl radicals, but also other substituents making possible a transfer to surfaces using the Langmuir-Blodgett (LB) and/or Langmuir-Blodgett-Schäfer (LBS) technique.

This layer can be applied by incubation in a solution, by a self assembly (SA) process or, preferably, using the Langmuir-Blodgett or Langmuir-Blodgett-Schäfer technique. The polysaccharide derivatives according to the invention can adhere both to hydrophilic and to hydrophobic surfaces. Thus, this class of substances can be applied and used as a surface-modifying film.

These layers are additionally stabilized by incorporating photopolymerizable or thermally polymerizable groups into the molecule(s), for example cinnamoyl groups, but also all other groups known in chemistry, since they stabilize the layer by crosslinking by polymerization before, during and after the transfer (the publications mentioned at the outset are expressly incorporated herein with their disclosure content).

The polymerizable groups can be attached here either at the abovementioned polysaccharide derivative or else be present in the form of a further molecule which is, mixed with the polysaccharide derivative, applied at or in the layer. The polymerization can take place within a monolayer; however, if a plurality of monolayers are present on top of each other, polymerization can also take place between molecules of the individual layers.

The polysaccharide derivatives according to the invention are used in various applications. Thus, they can be employed as "adhesion promoters" which are located between the surface of the carrier material and one or more other layers. Further layers can be applied using all known methods, but they are preferably applied using the Langmuir-Blodgett or Langmuir-Blodgett-Schäfer technique. Suitable further layers are, in particular, non-amphiphilic Haar-Stab polymers, especially polysaccharide-containing molecules, such as trialkylsilylcellulose itself, for example trimethylsilylcellulose cinnamoate, but also other derivatives.

A particularly important application of these, multicomponent layers is the use for immobilizing molecules at these surfaces. Here, at least the upper-most layer applied to the first layer acting as "adhesion promoter" has functional groups which allow other molecules to be bound covalently. These include, for example, amino groups, aldehyde groups, carboxylic acid derivatives and/or groups which can be converted into active groups, for example olefinic double bonds, cinnamic acid derivatives and the like.

Furthermore, this substance class is also suitable for direct coupling of molecules, owing to the aminoalkyl groups present. The aminoalkyl groups serve as nucleophilic agent and form covalent bonds with molecules carrying electrophilic groups.

If the molecules of the substance class mentioned have silyl groups, for example trialkyl-, triaryl- or trialkenylsilyl groups, the surface properties can be modified such that the silyl groups can be removed after coating, leaving hydroxyl groups behind. This can be effected, for example, by action of acid.

To summarize the embodiments of the process according to the invention which are preferred in each case the polysaccharide derivative is crosslinked before, during or after the coating is carried out, the coating is crosslinked, as a whole or in individual layers, by addition of a crosslinking agent, the coating comprises one or more individual layers, polysaccharide derivative is present in all layers outside the sheet-like carrier material, the layer comprising the polysaccharide derivative is the only coating, the layer comprising the polysaccharide derivative is an intermediate layer between the sheet-like carrier material and the coating, where the coating, if appropriate, also comprises polysaccharide derivative, biomolecules are attached to the polysaccharide derivative and the substituent b) of the polysaccharide derivative is removed after coating has been completed, and OH groups are re-established.

Very particular preference according to the invention is given to a process for immobilizing biomolecules on a carrier material in which the biomolecules are attached at or in the coating and the coating is carried out by LB, LBS or SA techniques, giving photochemically crosslinkable and non-amphiphilic molecules where the sheet-like carrier material comprises within or outside the coating at least one mixed cellulose ether according to the description above.

The mixed cellulose ethers according to the invention can be prepared in such a way that a solution of trialkylsilylcellulose in an organic solvent is admixed with a reactive aminoalkane derivative which is insoluble or only sparingly soluble in this solvent, the reaction is carried out and the end product is isolated.

EXAMPLES

Example 1

Synthesis of Aminopropyltrimethylsilylcellulose 1 g of trimethylsilylcellulose (Tmsc) is dissolved in a mixture of 50 ml of tetrahydrofuran (THF) and 6 ml of pyridine. 2 g of solid 1-amino-3-bromopropane are added to this solution. Polymerization of the 1-amino-3-bromopropane is suppressed by its poor solubility in THF, since the dissolved fraction reacts immediately. After a reaction time of 20 h at room temperature, the product is filtered off with suction, washed with methanol and water and recrystallized. The cellulose derivative is dissolved in chloroform (1 μg/1 μl) and spread on a water surface. At a surface pressure of 25 mN/m, it is finally transferred to a sheet-like carrier made of glass.

Example 2

Synthesis of Aminohexyltrimethylsilylcellulose 3.28 g of 6-aminohexanoic acid aredissolved in 40 ml of a 10% by weight strength aqueous $Na_2CO_3$ solution and 20 ml of dioxane. At 0° C., a solution of 6.47 g of 9-fluorenylmethyl chloroformate (for protecting the amino acid) in 45 ml of dioxane is added with stirring over a period of 15 min. The reaction product is added to 600 ml of $H_2O$ and extracted twice with 100 ml of diethyl ether each time. The aqueous phase is treated with HCl until the mixture reacts slightly acidic and is then extracted with in each case 200 ml of ethyl acetate, the organic phase is washed with $H_2O$ and dried with $MgSO_4$ and the solvent is removed.

1.04 g of 4-dimethylaminopyridine and 0.5 g of trimethylsilylcellulose are dissolved in 50 ml of methylene chloride. A suspension of the protected amino acid—which has been prepared as described above—in 40 ml of methylene chloride is then added rapidly, and 1.75 g of dicyclohexylcarbodiimide in 10 ml of methylene chloride are added dropwise. The reaction mixture is stirred at room temperature for 2 h and then concentrated, and the end product is precipitated out using 200 ml of methanol, washed with methanol and recrystallized from methylene chloride. The yield is 89%.

The resulting product can—in a similar manner to what was said in Example 1—be used by ramping, i.e. hydrodynamic flow at a surface, or by pulling out a substrate (for example glass) while keeping the surface pressure constant. With preference, the actual coating is applied to a monolayer ("adhesion promoter") produced in this way—as illustrated in detail above and exemplified by reference. Immobilization of biomolecules (i.e. molecules such as DNA, antibodies, antigenes, enzymes, hormones or other peptides) can be carried out successfully.

The structural formula below is meant to illustrate the products according to the invention by way of example; in FIG. 1, in the (mono)arminoalkyl(di)trialkylsilylcellulose, which is shown therein as being completely substituted at an anhydroglucose unit, m≧1 (preferably from 2 to 8)
$R^1$, $R^2$, $R^3$ are identical or different and are preferably $CH_3$ or $C_2H_5$
l is on average≧5.

What is claimed is:

1. A mixed cellulose ether comprising:
   (a) at least one trialkylsilyl group, wherein each alkyl radical independently has one or two carbon atoms, and
   (b) at least one aminoalkyl group, wherein each alkyl radical independently has two to eight carbon atoms; wherein the cellulose ether has a degree of polymerization of 5 and wherein the O atoms of a maximum of 3 OH groups on each cellulose skeleton are substituted by said trialkylsilyl group and aminoalkyl group.

2. A cellulose ether as claimed in claim 1, further comprising a substituent which carries a group which is crosslinkable photochemically, by a free-radical reaction or thermally.

3. A process for immobilizing biomolecules on a coated sheet-like carrier material comprising attaching the biomolecules at or in the coating, wherein the coated sheet-like carrier material comprises within or outside the coating at least one cellulose ether as claimed in claim 1.

4. A process as claimed in claim 3, further comprising coating the carrier material with the cellulose ether, and crosslinking the cellulose ether before, during or after the coating is carried out.

5. A process as claimed in claim 3, wherein the coating is crosslinked by addition of a crosslinking agent.

6. A process as claimed in claim 3, wherein the coating comprises one or more individual layers.

7. A process as claimed in claim 3, wherein the cellulose ether is present in all layers outside the sheet-like carrier material.

8. A process as claimed in claim 3, wherein the layer comprising the cellulose ether is the only coating.

9. A process as claimed in claim 3, wherein the layer comprising the cellulose ether is an intermediate layer between the sheet-like carrier material and the coating.

10. A process as claimed in claim 9, wherein the coating also comprises cellulose ether.

11. A process as claimed in claim 3, wherein biomolecules are attached to the cellulose ether.

12. A process as claimed in claim 3, further comprising removing the alkylamino group of the cellulose ether after coating has been completed, whereby OH groups are re-established.

13. A process for immobilizing biomolecules on a coated carrier material in which the biomolecules are attached at or in the coating, comprising coating the carrier material by an LB, LBS or SA technique, thereby providing photochemically crosslinkable and non-amphiphilic molecules, wherein the sheet-like carrier material comprises within or outside the coating at least one cellulose ether as claimed in claim 1.

14. A process for preparing the cellulose ether as claimed in claim 1, comprising admixing a solution of trialkylsilylcellulose in an organic solvent with a reactive aminoalkane derivative which is insoluble or only sparingly soluble in this solvent, carrying out a reaction, and isolating an end product.

15. A coated sheet-like carrier material having biomolecules immobilized at or in the coating, wherein the sheet-like carrier material comprises within or outside the coating at least one cellulose ether as claimed in claim 1.

16. A mixed cellulose ether of the formula:

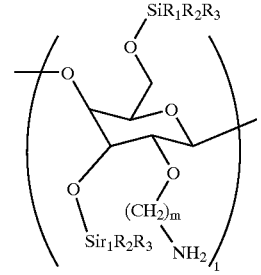

wherein m is from 2 to 8;
$R_1$, $R_2$, and $R_3$ are independently selected from $—CH_3$ and $—CH_2CH_3$; and
l is at least 5.

* * * * *